United States Patent [19]
Itoh et al.

[11] Patent Number: 5,919,985
[45] Date of Patent: *Jul. 6, 1999

[54] METHOD FOR PRODUCTION OF SULFIDE GROUP-CONTAINING THIOL COMPOUND

[75] Inventors: Hirokazu Itoh, Hyogo; Kazuaki Abe; Takashi Tomita, both of Osaka, all of Japan

[73] Assignees: Nippon Shokubai Co., Ltd., Japan; Elf Atochem SA, France

[ * ] Notice: This patent is subject to a terminal disclaimer.

[21] Appl. No.: 08/987,402

[22] Filed: Dec. 9, 1997

[30] Foreign Application Priority Data

Jan. 17, 1997 [JP] Japan ................................. 9-006960

[51] Int. Cl.$^6$ ................................................. C07C 319/06
[52] U.S. Cl. ............................... 568/63; 568/39; 568/41; 568/57; 568/59; 568/67; 560/152
[58] Field of Search .................. 568/39, 38, 41, 568/59, 57, 63, 66, 67; 560/152; 528/66, 67

[56] References Cited

U.S. PATENT DOCUMENTS

| | | |
|---|---|---|
| 2,490,984 | 12/1949 | Snyder et al. . |
| 2,497,100 | 2/1950 | Snyder et al. . |
| 3,544,543 | 12/1970 | Greco . |
| 4,163,832 | 8/1979 | Oswald ..................................... 528/76 |
| 4,355,185 | 10/1982 | Bergthaller . |

FOREIGN PATENT DOCUMENTS

| | | |
|---|---|---|
| 696 774 | 9/1940 | Germany . |
| 471067 | 1/1972 | Japan . |

OTHER PUBLICATIONS

European Search Report, May 14, 1998.

Fokin et al., "Reaction For Nucleophilic Opening of Thiirane Ring by Thiols", *Bulletin Acad. Sci. of USSR. Div. Chem. Sci.*, 24:582–584, 1975.

Culvenor et al., The Preparation and Reactions of Aliphatic and Alicyclic Ethylene Sulphides, J. Chem. Soc., pp. 282–287, 1949.

Fokin et al., Reaction for Nucleophilic Opening of Thiirane Ring by Thiols, Translated from Izvestiya Akademii Nauk SSSR, Seriya Khimicheskaya, No. 3, pp. 660–662, Mar. 1975.

Meade and Woodward, Some Reactions of Ethylene Sulphide, and a New Method of Preparation of Vicinal Meade and Woodward, Some Reactions of Ethylene Sulphide, and a new Method of Preparation of Vicinal Dithiols, J. Chem. Soc., pp. 1894–1895, 1948.

Snyder et al., The Synthesis of Mercaptans from Olefin Sulfides, J.A.C.S. 69:2675–2677, 1947.

*Primary Examiner*—Gary Geist
*Assistant Examiner*—Jean F. Vollano
*Attorney, Agent, or Firm*—Fish & Richardson PC

[57] ABSTRACT

An object is to provide a method for the production of a sulfide group-containing thiol compound which comprises using a solvent capable of effecting the ring-opening addition reaction of an alkylene sulfide to a thiol compound without inducing the alkylene sulfide to polymerize. A method for the production of a sulfide group-containing thiol compound, which comprises effecting the ring-opening addition reaction of an alkylene sulfide represented by the general formula (1):

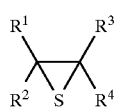

(1)

(wherein $R^1$, $R^2$, $R^3$, and $R^4$, which may be identical or different, stand for a hydrogen atom, an alkyl group of 1 to 10 carbon atoms, or an aromatic group of 6 to 15 carbon atoms) to a thiol compound in a solvent of an amide compound or urea substituent-containing compound.

7 Claims, No Drawings

METHOD FOR PRODUCTION OF SULFIDE GROUP-CONTAINING THIOL COMPOUND

BACKGROUND OF THE INVENTION

1. Field of the Invention

This invention relates to a method for the production of a sulfide group-containing thiol compound. More particularly, it relates to a method for the production of a sulfide group-containing thiol compound by the ring-opening addition of an alkylene sulfide to a thiol compound.

The sulfide group-containing thiol compounds which are obtained by the method of this invention are useful compounds which find extensive utility in a chelating agent, a lubricant additive, an additive for rubber, an additive for the oil refining treatment, a polymerization chain transfer agent, and etc.

2. Description of the Related Art

As respects methods for producing a sulfide group-containing thiol compound by the ring-opening addition of an alkylene sulfide to a thiol compound, a method for causing this reaction without using a catalyst was disclosed long ago in German Patent No. 696,774. This method, however, necessitates an elevated temperature. To solve this problem, U.S. Pat. No. 2,490,984 and U.S. Pat. No. 2,497,100 propose methods which use sodium alkoxide and boron trifluoride respectively as a catalyst. Further, methods using alkali metal alkoxides as a catalyst are disclosed in J. Am. Chem. Soc. (1947), Vol. 69, p. 2675, J. Chem. Soc. (1948), p. 1894, and J. Chem. Soc. (1949), p. 282. Though these catalysts have high activity, they have the problem of manifesting low selectivity for the products aimed at because the alkylene sulfides themselves as a raw material are liable to be polymerize.

Izv. Akad. Nauk. SSSR, Ser. Khim. (1975), No. 3, p. 660 and U.S. Pat. No. 4,163,832 discloses a method which uses amine compounds such as trimethyl amine and triethyl amine or trimethyl phosphine as a catalyst. JP-B-07-5,585 discloses a method which effects the reaction in an aqueous sodium hydroxide solution-benzene system using benzyl trimethyl ammonium chloride as a catalyst. The methods mentioned above are invariably liable to induce the polymerization of alkylene sulfide as a secondary reaction and, particularly when ethylene sulfide is used as a raw material, incur difficulty in preventing the ethylene sulfide from being polymerized.

As described above, although numerous reports published to date have covered methods for obtaining a sulfide group-containing thiol compound by the ring-opening addition of an alkylene sulfide to a thiol compound, these methods have intolerable defects. A method capable of selectively producing a sulfide group-containing thiol compound aimed at has not yet been brought into being.

An object of this invention, therefore, it to provide a novel method for producing a sulfide group-containing thiol compound.

Another object of this invention is to provide a method for producing a sulfide group-containing thiol compound with high selectivity without entailing polymerization of alkylene sulfide.

Yet another object of this invention is to provide a method for producing a sulfide group-containing thiol compound using a solvent capable of effecting the ring-opening addition reaction with high selectivity without inducing the polymerization of alkylene sulfide.

SUMMARY OF THE INVENTION

The present inventors, as a result of making a diligent study in search of a novel method for producing a sulfide group-containing compound without entailing the problems mentioned above, have found that a sulfide group-containing thiol compound can be produced with high selectivity by using as a solvent an amide compound or an urea substituent-containing compound and effecting the ring-opening addition reaction of an alkylene sulfide to a thiol compound in this solvent. The present invention has been perfected based on this knowledge.

To be specific, the objects mentioned above can be attained by a method for the production of a sulfide group-containing thiol compound, which comprises effecting the ring-opening addition reaction of an alkylene sulfide represented by the general formula (1):

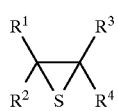

(1)

(wherein $R^1$, $R^2$, $R^3$, and $R^4$, which may be identical or different, stand for a hydrogen atom, an alkyl group of 1 to 10 carbon atoms, or an aromatic group of 6 to 15 carbon atoms) to a thiol compound in a solvent of an amide compound or an urea substituent-containing compound.

As described above, the method for the production of a sulfide group-containing thiol compound of this invention is characterized by subjecting an alkylene sulfide represented by the general formula (1) to the ring-opening addition reaction to a thiol compound in a solvent of an amide compound or an urea substituent-containing compound. According to the method of this invention, therefore, the sulfide group-containing thiol compound can be produced by effecting the ring-opening addition of an alkylene sulfide to the thiol compound with high selectivity. Particularly when ethylene sulfide is used as the alkylene sulfide, since the formation of an insoluble polymer can be repressed, the work for removing the insoluble polymer as by filtration is no longer required and the efficiency of production can be improved.

DESCRIPTION OF THE PREFERRED EMBODIMENT

For the production of a sulfide group-containing thiol compound by the ring-opening addition of an alkylene sulfide to a thiol compound according to this invention, it is essential to use an amide compound or an urea substituent-containing compound as a solvent.

As the amide compound to be used as the solvent in this invention, the compounds which are represented by the general formula (2):

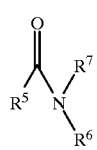

(2)

(wherein $R^5$, $R^6$, and $R^7$, which may be identical or different, stand for a hydrogen atom, an alkyl group of 1 to 4 carbon atoms, or an alkylene group of 2 to 4 carbon atoms having $R^5$ and $R^6$ bound each other), for example, may be appropriately used.

As typical examples of the amide compounds represented by the general formula (2) mentioned above, formamide, N-methyl formamide, N,N-dimethyl formamide, N-ethyl formamide, N,N-diethyl formamide, N,N-di-n-propyl formamide, N,N-diisopropyl formamide, N-n-butyl formamide, N-tert-butyl formamide, N,N-di-n-butyl formamide, acetamide, N-methyl acetamide, N,N-dimethyl acetamide, N-ethyl acetamide, N,N-diethyl acetamide, N,N-di-n-propyl acetamide, N,N-diisopropyl acetamide, N-n-butyl acetamide, N-tert-butyl acetamide, N,N-di-n-butyl acetamide, propione amide, N-methyl propione amide, N,N-dimethyl propione amide, N-ethyl propione amide, N,N-diethyl propione amide, N,N-diisopropyl propione amide, N-n-butyl propione amide, N-tert-butyl propione amide, N,N-di-n-butyl propione amide, 2-methyl propione amide, N-methyl-2-methyl propione amide, N,N-dimethyl-2-methyl propione amide, N-ethyl-2-methyl propione amide, N,N-diethyl-2-methyl propione amide, N, N-di-n-propyl-2-methyl propione amide, N, N-diisopropyl-2-methyl propione amide, N-n-butyl-2-methyl propione amide, N-tert-butyl-2-methyl propione amide, N, N-di-n-butyl-2-methyl propione amide, 2-pyrrolidone, 1-methyl-2-pyrrolidone, 1-ethyl-2-pyrrolidone, 1-n-propyl-1-pyrrolidone, 1-isopropyl-2-pyrrolidone, 1-n-butyl-2-pyrrolidone, 2-piperidone, 1-methyl-2-piperidone, 1-ethyl-2-piperidone, 1-n-propyl-2-piperidone, 1-isopropyl-2-piperidone, and 1-n-butyl-2-piperidone may be cited. Among the compounds mentioned above, N,N-dimethyl formamide, N,N-diethyl formamide, N,N-dimethyl acetamide, N,N-diethyl acetamide, 1-methyl-2-pyrrolidone, and 1-methyl-2-piperidone may be used particularly advantageously.

As the urea substituent-containing compound to be used as the solvent in this invention, the compounds which are represented by the general formula (3):

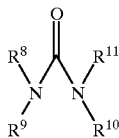

(3)

(wherein $R^8$, $R^9$, $R^{10}$, and $R^{11}$, which may be identical or different, stand for a hydrogen atom, an alkyl group of 1 to 4 carbon atoms, or an alkylene group of 2 or 3 carbon atoms having $R^9$ and $R^{10}$ bound mutually), for example, may be advantageously used.

As typical examples of the urea substituent-containing compounds represented by the general formula (3) above, 1,1,3,3-tetramethyl urea, 1,1,3,3-tetraethyl urea, 1,1,3,3-tetra-n-propyl urea, 1,1,3,3-tetraisopropyl urea, 1,1,3,3-tetra-n-butyl urea, ethylene urea, N,N'-trimethylene urea, N,N'-dimethyl propylene urea, and 1,3-dimethyl-2-imidazolidinone may be cited. Among the urea substituent-containing compounds mentioned above, 1,1,3,3-tetramethyl urea, N,N'-dimethyl propylene urea, and 1,3-dimethyl-2-imidazolidinone may be used particularly advantageously.

Though the amount of the solvent mentioned above to be used in the execution of the reaction according to this invention is not particularly limited, it is generally in the range of 10 to 1,000 parts by weight, preferably 50 to 500 parts by weight, based on 100 parts by weight of the thiol compound. If the amount of the solvent used is less than 10 parts by weight, the disadvantage ensues that the effect of repressing the polymerization of an alkylene sulfide will not be manifested fully satisfactorily. Conversely, if this amount exceeds 1,000 parts by weight, the excess, if not detrimental to the reaction, will impair the economy of the reaction. In this invention, the solvents mentioned above may be used either singly or in the form of a combination of two or more members. Such an use of the solvent can represses efficiently the polymerization of an alkylene sulfide during the course of the reaction and improve the selectivity of the reaction for the product aimed at.

Further, in the present invention, the polymerization of an alkylene sulfide can be curbed, the reaction velocity increased, and the productivity of the reaction improved by using an amine compound as a catalyst in combination with the solvent mentioned above. As the amine compound which is used as the catalyst in the reaction according to this invention, a tertiary amine compound proves to be appropriate.

As typical examples of the amine compound to be used as the catalyst in this invention, alkyl tertiary amines such as trimethyl amine, triethyl amine, tri-n-propyl amine, triisopropyl amine, tri-n-butyl amine, tri-n-octyl amine, N-ethyl diisopropyl amine, and N,N-dimethyl-n-dodecyl amine; alkylene polyamines such as N,N,N',N'-tetramethyl ethylene diamine, N,N,N',N'-tetramethyl-1,3-diamino propane, N,N,N',N'-tetramethyl-1,4-diamino butane, N,N,N',N'-tetramethyl-1,6-diamino hexane, and N,N,N',N'-pentamethyl diethylene triamine; N-methyl morpholine, N-methyl piperidine, 1,4-dimethyl piperazine, N,N-dimethylbenzyl amine, 2,4,6-tris(dimethylamiomethyl) phenol, N,N-dimethyl aniline, N,N-diethyl aniline, 1,4-diazabicyclo[2.2.2]octane, 1,8-diazabicyclo[5.4.0]undecene, N,N-dimethyl ethanol amine, N,N-diethyl ethanol amine, triethanol amine, hexamethylene tetramine, pyridine, picoline, lutidine, quinoline, isoquinoline, pyrazine, and 4-dimethyl amino pyridine may be cited.

Though the amount of the catalyst mentioned above to be used in the execution of the reaction in accordance with this invention is not particularly limited, it is generally in the range of 0.01 to 10 parts by weight, preferably 0.1 to 5 parts by weight, based on 100 parts by weight of the thiol compound. If the amount of the catalyst to be used is less than 0.01 part by weight, the disadvantage ensues that the reaction velocity will be lowered. Conversely, if this amount exceeds 10 parts by weight, the excess, if not detrimental to the reaction, will impair the economy of the reaction. Though the method for using the catalyst mentioned above is varied with the mode of the reaction, the catalyst may be collectively added at the outset of the reaction or successively added during the course of the reaction. The catalysts cited above may be used in this invention either singly or in the form of a combination of two or more members.

The alkylene sulfides to be used as the raw material in the present invention are the compounds represented by the general formula (1):

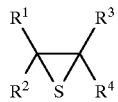

(1)

In the formula (1) shown above, $R^1$, $R^2$, $R^3$, and $R^4$, which may be identical or different, stand for a hydrogen atom, an alkyl group of 1 to 10, preferably 1 to 6, carbon atoms, or an aromatic group of 6 to 15, preferably 6 to 10, carbon atoms.

As typical examples of the alkylene sulfides to be used in this invention, ethylene sulfide, propylene sulfide, isobutylene sulfide, and styrene sulfide may be cited. Among the alkylene sulfides mentioned above, ethylene sulfide and propylene sulfide prove advantageous. Ethylene sulfide may be especially advantageous because the effect of this invention is prominently manifested when ethylene sulfide is used.

Though the thiol compound to be used as the raw material in this invention is not particularly limited, compounds which are selected from the group consisting of alkane thiols, aromatic thiols, alkyl thiocarboxylic acids, aromatic thiocarboxylic acids, mercaptoalkanoic esters, and mercaptoalkanols may be used appropriately. These compounds are mainly such compounds as are represented by the general formula (4):

$$R^{12}SH \quad (4)$$

In the formula (4) given above, $R^{12}$ stands for an alkyl group of 1 to 20, preferably 1 to 12, carbon atoms, an aromatic group of 6 to 20, preferably 6 to 12, carbon atoms, or $R^{13}CO—$, wherein $R^{13}$ stands for an alkyl group of 1 to 20, preferably 1 to 8, carbon atoms, or an aromatic group of 6 to 20, preferably 6 to 12, carbon atoms.

When the thiol compound in this invention is to be a mercaptoalkanoic ester, examples of the mercaptoalkanoic ester used appropriately herein are such compounds as are represented by the following general formula (5):

$$R^{14}O—CO—R^{15}—SH \quad (5)$$

In the formula (5) given above, $R^{14}$ stands for an alkyl group of 1 to 20, preferably 1 to 12, carbon atoms and $R^{15}$ stands for an alkylene group of 1 to 4, preferably 1 or 2, carbon atoms.

As typical examples of the thiol compound to be used in this invention, alkane thiols such as methane thiol, ethane thiol, propane thiol, butane thiol, hexane thiol, and octane thiol; polythiols such as ethane dithiol, propane dithiol, butane dithiol, and bis(2-mercaptoethyl)sulfide; aromatic thiols such as thiophenol, 1,2-benzene dithiol, 1,4-benzene dithiol, and 4-mercapto phenol; mercaptoalkanols such as 2-mercapto ethanol, 3-mercapto propanol, 1-methyl-2-mercapto ethanol, and thioglycerol; mercaptoalkanoic esters such as methyl ester, ethyl ester, propyl ester, butyl ester, hexyl ester, n-octyl ester, isooctyl ester, 2-ethylhexyl ester, lauryl ester, stearyl ester, ethylene glycol ester, glycerin ester, trimethylol propane ester, pentaerythritol ester, and dipentaerythritol ester of 3-mercapto propionic acid, methyl ester, ethyl ester, n-propyl ester, isopropyl ester, n-butyl ester, isobutyl ester, tert-butyl ester, n-hexyl ester, n-octyl ester, isooctyl ester, 2-ethylhexyl ester, n-dodecyl ester, stearyl ester, ethylene glycol ester, glycerin ester, trimethylol propane ester, pentaerythritol ester, and dipentaerythritol ester of 2-mercapto propionic acid, and methyl ester, ethyl ester, n-propyl ester, isopropyl ester, n-butyl ester, isobutyl ester, tert-butyl ester, n-hexyl ester, n-octyl ester, isooctyl ester, 2-ethylhexyl ester, n-dodecyl ester, stearyl ester, ethylene glycol ester, glycerin ester, trimethylol propane ester, pentaerythritol ester, and dipentaerythritol ester of 2-mercapto acetic acid; thiocarboxylic acids such as thioacetic acid, thiopropionic acid, thiobutyric acid, and thiobenzoic acid; and allyl mercaptan, benzyl mercaptan, and furfuryl mercaptan may be cited. Among other thiol compounds mentioned above, mercaptoalkanoic esters, mercaptoalkanols, aromatic thiols, aromatic thiocarboxylic acids, and alkane thiols prove particularly appropriate. The effect of this invention is conspicuously manifested when mercaptoalkanoic esters are used.

For the purpose of sufficiently repressing the polymerization of the alkylene sulfide in the ring-opening addition reaction of the alkylene sulfide to the thiol compound in accordance with the present invention, the reaction appropriately may be carried out with the amount of the alkylene sulfide kept at or below 2 mols per mol of the thiol compound. Particularly when ethylene sulfide is adopted for the ring-opening addition reaction to the thiol compound according to this invention, the amount of ethylene sulfide to be used is preferably not more than 1.5 mols, more preferably not more than 1 mol, per mol of the thiol compound. The procedure of carrying out the reaction while successively adding the alkylene sulfide to the reaction system may be appropriately used because it enables the effect of repressing the polymerization of the alkylene sulfide to be manifested more conspicuously and the removal of the heat of reaction to be effected easily.

The reaction temperature in the method of this invention is generally in the range of 0° to 200° C., preferably 10° to 150° C. When the amine compound as a catalyst is incorporated in the reaction system according this invention, this reaction can proceed fully satisfactorily even at or below room temperature. The reaction pressure in the method of this invention, though not particularly limited, generally is in the range of 1 to 100 kg/cm², preferably 1 to 20 kg/cm². For the purpose of preventing the thiol group from being oxidized with oxygen during the course of the reaction, it is appropriate for the interior of the reaction system to be retained under an atmosphere of an inert gas. As typical examples of the insert gas to be used herein, nitrogen, argon, and helium may be cited.

By carrying out the reaction described above, a sulfide group-containing thiol compound represented by the general formula (6):

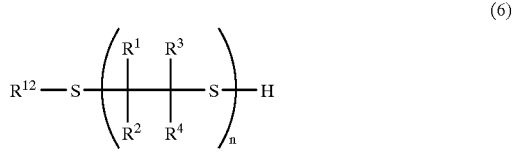

(wherein $R^1$, $R^2$, $R^3$, $R^4$, and $R^{12}$ are as defined above and n is an integer in the range of 1 to 6, preferably 1 to 3) can be obtained.

Now, this invention will be described more specifically below with reference to working examples and controls. It should be noted, however, that the scope of this invention is not limited thereto.

EXAMPLE 1

In a four-neck flask provided with a stirrer, a reflux condenser, a thermometer, and a dropping funnel, 60.1 g (0.5 mol) of methyl 3-mercapto propionate and 60.1 g of 1-methyl-2-pyrrolidone were placed and kept swept with a stream of nitrogen and heated at 50° C. and 6.0 g (0.1 mol) of ethylene sulfide was drop-fed thereto over a period of 20 minutes. At the same temperature, they were left reacting further for three hours. When the reaction product was subsequently extracted from the flask, it was found to have formed absolutely no insoluble precipitate of a polymer of ethylene sulfide. When this reaction product was analyzed by gas chromatography, it was found to have formed a 1-mol adduct and a 2-mol adduct of ethylene sulfide at a ratio of 88:12 (the ratio of areas on a gas chromatogram). The total yield based on ethylene sulfide was 96%. The results are shown in Table 1 and Table 2.

EXAMPLE 2

When the reaction was carried out by following the procedure of Example 1 while using 30.0 g of N,N-dimethyl formamide in place of 1-methyl-2-pyrrolidone, the results shown in Table 1 and Table 2 were obtained.

EXAMPLE 3

When the reaction was carried out by following the procedure of Example 1 while using 30.0 g of N,N-dimethyl acetamide in place of 1-methyl-2-pyrrolidone, the results shown in Table 1 and Table 2 were obtained.

EXAMPLE 4

When the reaction was carried out by following the procedure of Example 1 while using 60.1 g of 1,3-dimethyl-2-imidazolidinone in place of 1-methyl-2-pyrrolidone, the results shown in Table 1 and Table 2 were obtained.

EXAMPLE 5

When the reaction was carried out by following the procedure of Example 1 while using as the solvent 30.0 g of N,N-dimethyl formamide in place of 1-methyl-2-pyrrolidone and using as the catalyst 0.90 g of triethyl amine, the results shown in Table 1 and Table 2 were obtained.

EXAMPLE 6

When the reaction was carried out by following the procedure of Example 1 while using as the solvent 30.0 g of N,N-dimethyl acetamide in place of 1-methyl-2-pyrrolidone and using as the catalyst 0.90 g of triethyl amine, the results shown in Table 1 and Table 2 were obtained.

EXAMPLE 7

When the reaction was carried out by following the procedure of Example 1 while using as the solvent 30.0 g of N,N-dimethyl formamide in place of 1-methyl-2-pyrrolidone and using as the catalyst 0.54 g of tri-n-octyl amine, the results shown in Table 1 and Table 2 were obtained.

EXAMPLE 8

When the reaction was carried out by following the procedure of Example 1 while changing the amounts of methyl 3-mercapto propionate and 1-methyl-2-pyrrolidone to be added respectively to 48.1 g (0.4 mol) and 96.2 g (0.8 mol) and using as the catalyst 0.24 g of tri-n-butyl amine, the results shown in Table 1 and Table 2 were obtained.

EXAMPLE 9

When the reaction was carried out by following the procedure of Example 1 while using 52.1 g (0.2 mol) of n-dodecyl 2-mercapto acetate as the thiol compound in place of methyl 3-mercapto propionate, 52.1 g of 1,3-dimethyl-2-imidazolidinone as the solvent in place of 1-methyl-2-pyrrolidone, and additionally using 0.52 g of N,N,N',N'-tetramethyl ethylene diamine as the catalyst, the results shown in Table 1 and Table 2 were obtained.

EXAMPLE 10

When the reaction was carried out by following the procedure of Example 1 while using 23.4 g (0.3 mol) of 2-mercapto ethanol as the thiol compound in place of methyl 3-mercapto propionate, changing the amount of 1-methyl-2-pyrrolidone to be added to 23.4 g, and additionally using 0.23 g of N-methyl morpholine as the catalyst, the results shown in Table 1 and Table 2 were obtained.

EXAMPLE 11

When the reaction was carried out by following the procedure of Example 1 while using 22.0 g (0.2 mol) of thiophenol as the thiol compound in place of methyl 3-mercapto propionate, 22.0 g of N-methyl acetamide as the solvent in place of 1-methyl-2-pyrrolidone, and additionally using 0.22 g of pyridine as the catalyst, the results shown in Table 1 and Table 2 were obtained.

EXAMPLE 12

When the reaction was carried out by following the procedure of Example 1 while using 7.6 g (0.1 mol) of thioacetic acid as the thiol compound in place of methyl 3-mercapto propionate, 38.0 g of 1,1,3,3-tetramethyl urea as the solvent in place of 1-methyl-1-pyrrolidone, and additionally using 0.04 g of N,N-dimethyl aniline as the catalyst, the results shown in Table 1 and Table 2 were obtained.

EXAMPLE 13

When the reaction was carried out by following the procedure of Example 1 while using 13.8 g (0.1 mol) of thiobenzoic acid as the thiol compound in place of methyl-3-mercapto propionate, 13.8 g of N,N-dimethyl formamide as the solvent in place of 1-methyl-2-pyrrolidone, 7.4 g (0.1 mol) of propylene sulfide as the alkylene sulfide in place of ethylene sulfide, and additionally using 0.14 g of N,N-dimethyl aniline as the catalyst, the results shown in Table 1 and Table 2 were obtained.

TABLE 1

| Example | Thiol compound (A) | Alkylene sulfide (B) | Molar ratio of raw materials (A)/(B) | Solvent | Amount of solvent added (wt % based on thiol compound) |
|---|---|---|---|---|---|
| 1 | Methyl 3-mercapto propionate | ES | 5/1 | 1-Methyl-2-pyrrolidone | 100 |
| 2 | Methyl 3-mercapto propionate | ES | 5/1 | N,N-dimethyl formamide | 50 |
| 3 | Methyl 3-mercapto propionate | ES | 5/1 | N,N-dimethyl acetamide | 50 |
| 4 | Methyl 3-mercapto propionate | ES | 5/1 | 1,3-Dimethyl-2-imidazolidinone | 100 |
| 5 | Methyl 3-mercapto propionate | ES | 5/1 | N,N-Dimethyl formamide | 50 |
| 6 | Methyl 3-mercapto propionate | ES | 5/1 | N,N-Dimethyl acetamide | 50 |
| 7 | Methyl 3-mercapto propionate | ES | 5/1 | N,N-Dimethyl formamide | 50 |
| 8 | Methyl 3-mercapto propionate | ES | 4/1 | 1-Methyl-2-pyrrolidone | 200 |
| 9 | n-Dodecyl 2-mercapto acetate | ES | 2/1 | 1,3-Dimethyl-2-imidazolidinone | 100 |
| 10 | 2-Mercapto ethanol | ES | 3/1 | 1-Methyl-2-pyrrolidone | 100 |
| 11 | Thiophenol | ES | 2/1 | N-Methyl acetamide | 100 |
| 12 | Thioacetic acid | ES | 1/1 | 1,1,3,3-Tetramethyl urea | 500 |
| 13 | Thiobenzoic acid | PS | 1/1 | N,N-Dimethyl formamide | 100 |

Abbreviation)
ES: Ethylene sulfide;
PS: Propylene sulfide;

TABLE 2

| Example | Catalyst | Amount of catalyst added (wt % based on thiol compound) | Total yield of product (%) | Ratio of product | | | Presence of ethylene sulfide polymers (insoluble materials) |
|---|---|---|---|---|---|---|---|
| | | | | 1-mol adduct | 2-mol adduct | 3-mol adduct | |
| 1 | — | — | 96 | 88 | 12 | 0 | None |
| 2 | — | — | 90 | 90 | 10 | 0 | None |
| 3 | — | — | 82 | 91 | 9 | 0 | None |
| 4 | — | — | 73 | 89 | 11 | 0 | None |
| 5 | Triethyl amine | 1.5 | 97 | 90 | 10 | 0 | None |
| 6 | Triethyl amine | 1.5 | 98 | 87 | 13 | Trace amount | None |
| 7 | Tri-n-octyl amine | 0.9 | 97 | 88 | 12 | 0 | None |
| 8 | Tri-n-butyl amine | 0.5 | 96 | 89 | 11 | 0 | None |
| 9 | N,N,N',N'-Tetramethyl ethylene diamine | 1.0 | 98 | 99 | 1 | 0 | None |
| 10 | N-Methyl morpholine | 1.0 | 95 | 83 | 16 | 1 | None |
| 11 | Pyridine | 1.0 | 96 | 96 | 4 | 0 | None |
| 12 | N,N-Dimethyl aniline | 0.5 | 89 | 95 | 5 | 0 | None |
| 13 | N,N-Dimethyl aniline | 1.0 | 83 | 98 | 2 | 0 | — |

Control 1

The reaction was carried out by following the procedure of Example 1 while using 60.1 g (0.5 mol) of methyl 3-mercapto propionate as the thiol compound and 0.90 g of triethyl amine as the catalyst and omitting the use of a solvent.

In the initial stage of the drop-feeding of ethylene sulfide, the ethylene sulfide was polymerized to such an extent as of opacity of the reaction solution. Thus, the reaction was discontinued in an unfinished state.

The entire disclosure of Japanese Patent Application No. 09-006960 filed on Jan. 17, 1997 including specification, claims, drawings and summary are incorporated herein by reference in its entirety.

What is claimed is:

1. A method for the production of a sulfide group-containing thiol compound, which comprises carrying out the ring-opening addition reaction of an alkylene sulfide represented by the general formula (1):

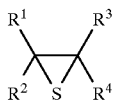

(1)

(wherein $R^1$, $R^2$, $R^3$, and $R^4$, which may be identical or different, stand for a hydrogen atom, an alkyl group of 1 to 10 carbon atoms, or an aromatic group of 6 to 15 carbon atoms) to a thiol compound represented by the general formula (4) $R^{12}SH$ in a solvent of an amide compound or an urea substituent-containing compound, to produce the sulfide group-containing thiol compound represented by the general formula (6):

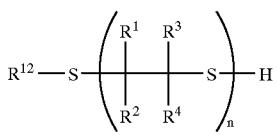

(6)

(wherein $R^1$, $R^2$, $R^3$, and $R^4$, are as defined above, $R^{12}$ stands for an alkyl group of 1 to 20 carbon atoms, an aromatic group of 6 to 20 carbon atoms, $R^{13}CO$— where $R^{13}$ stands for an alkyl group of 1 to 20 carbon atoms or an aromatic group of 6 to 20 carbon atoms, or $R^{14}O$—CO—$R^{15}$—, wherein $R^{14}$ stands for an alkyl group of 1 to 20 carbon atoms and R15 stands for an alkylene group of 1 to 4 carbon atoms, and n is an integer in the range of 1 to 6).

2. A method according to claim 1, wherein the reaction is carried out in the presence of an amine compound as a catalyst.

3. A method according to claim 1, wherein said amide compound is a compound represented by the general formula (2):

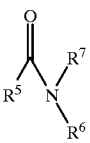

(2)

(wherein $R^5$, $R^6$, and $R^7$, which may be identical or different, stand for a hydrogen atom, an alkyl group of 1 to 4 carbon atoms, or an alkylene group of 2 to 4 carbon atoms having $R^5$ and $R^6$ bound each other) and said urea substituent-containing compound is a compound represented by the general formula (3):

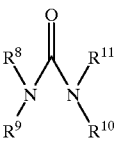

(3)

(wherein $R^8$, $R^9$, $R^{10}$, and $R^{11}$, which may be identical or different, stand for a hydrogen atom, an alkyl group of 1 to 4 carbon atoms, or an alkylene group of 2 or 3 carbon atoms having $R^9$ and $R^{10}$ bound mutually).

4. A method according to claim 2, wherein said amine compound is a tertiary amine.

5. A method according to claim 1, wherein said thiol compound is one member selected from the group consisting of alkane thiols, aromatic thiols, alkyl thiocarboxylic acids, aromatic thiocarboxylic acids, mercaptoalkanoic esters, and mercaptoalkanols.

6. A method according to claim 1, wherein said alkylene sulfide is ethylene sulfide or propylene sulfide.

7. A method according to claim 1, wherein the amount of said amide compound or urea substituent-containing compound is in the range of 10 to 1,000 parts by weight, based on 100 parts by weight of the thiol compound.

* * * * *